(12) United States Patent
Nguyen (10) Patent No.: US 9,895,554 B2
(45) Date of Patent: Feb. 20, 2018

(54) IMAGE-GUIDED RADIOTHERAPY FOR INTERNAL TUMOR BOOST

(71) Applicant: Nam Nguyen, Washington, DC (US)

(72) Inventor: Nam Nguyen, Washington, DC (US)

( * ) Notice: Subject to any disclaimer, the term of this patent is extended or adjusted under 35 U.S.C. 154(b) by 57 days.

(21) Appl. No.: 14/436,394

(22) PCT Filed: Oct. 16, 2013

(86) PCT No.: PCT/US2013/065283
§ 371 (c)(1),
(2) Date: Apr. 16, 2015

(87) PCT Pub. No.: WO2014/062830
PCT Pub. Date: Apr. 24, 2014

(65) Prior Publication Data
US 2015/0246246 A1   Sep. 3, 2015

Related U.S. Application Data

(63) Continuation-in-part of application No. 13/652,821, filed on Oct. 16, 2012, now abandoned.

(51) Int. Cl.
*A61N 5/10* (2006.01)

(52) U.S. Cl.
CPC .......... *A61N 5/1049* (2013.01); *A61N 5/1031* (2013.01); *A61N 5/1064* (2013.01)

(58) Field of Classification Search
CPC .... A61N 2005/1089; A61N 2005/1091; A61N 5/103; A61N 5/1049; A61N 5/1084; A61N 5/1031; A61N 5/1064
See application file for complete search history.

(56) References Cited

U.S. PATENT DOCUMENTS

| | | | | |
|---|---|---|---|---|
| 7,606,405 | B2 * | 10/2009 | Sawyer | A61N 5/1049 378/65 |
| 8,173,983 | B1 * | 5/2012 | Sahadevan | A61N 5/1084 250/341.7 |
| 8,238,520 | B2 | 8/2012 | Nord et al. | |
| 2005/0041843 | A1 * | 2/2005 | Sawyer | A61N 5/1049 382/128 |
| 2006/0067469 | A1 | 3/2006 | Dooley et al. | |
| 2007/0014454 | A1 | 1/2007 | Sawyer et al. | |
| 2009/0130098 | A1 | 5/2009 | Goodman et al. | |
| 2010/0228116 | A1 | 9/2010 | Lu et al. | |
| 2010/0322381 | A1 | 12/2010 | Stahl et al. | |

(Continued)

OTHER PUBLICATIONS

Sause, WT et al.; Fraction size in external beam radiation therapy in the treatment of melanoma; Int J Radiat Oncol Biol Phys; Mar. 1991; 20(3):429-32 (Abstract).

(Continued)

*Primary Examiner* — Christine H Matthews (57) ABSTRACT

An image-guided radiotherapy system for tumor treatment featuring obtaining a three-dimensional visualized tumor image, identifying the boundary of the tumor, and designating and applying a boosted radiation dose of treatment for a boost region within the tumor boundary. A predetermined safety region is between the boosted region and the tumor boundary with a predetermined minimum distance between the boosted region boundary and tumor boundary.

2 Claims, 8 Drawing Sheets

(56) References Cited

U.S. PATENT DOCUMENTS

2011/0075806 A1   3/2011   Nord et al.
2012/0326057 A1   12/2012  Remeijer et al.

OTHER PUBLICATIONS

Radiation Therapy Oncology Group, RTOG 0920, A Phase III Study of Postoperative Radiation Therapy (IMRT) +/- Cetuximab For Locally Advanced Resected Head And Neck Cancer, Dec. 6, 2010 Nancy Lee, M.D, Adam Garden, M.D., Alan Kramer, M.D, Ping Xia, Ph.D., Radiation Therapy Oncology Group, RTOG 0225: A Phase II Study Of Intensity Modulated Radiation Therapy (IMRT) +/- Chemotherapy For Nasopharyngeal Cancer, May 26, 2005.
Schofield, Debbie et al., Review and guidelines for treating head and neck tumors using IMRT and VMAT, AAPM 2010.
Schofield, Debbie; Farber, Dana, "The Use of IMRT in the Treatment of Head and Neck Cancer"; 2012.
Mayo, Charles; "Review and guidelines for treating head and neck tumors using IMRT and VMAT"; 2012.

\* cited by examiner

| Structure | Clinical Dose Limits | Inverse Planning Algorithm Constraint Template | | | |
|---|---|---|---|---|---|
| | | Prescription Dose (%) | Maximum Dose (%) /Penalty | Minimum Dose (%) /Penalty | Dose (%)-%Volume Constraint/Penalty |
| $PTV_{el}$ | $D_{95} \geq 50$ Gy (95% of 54 Gy) Max. Dose $\leq 64.8$ Gy (120% of 54 Gy) | 54 Gy (77%) | 56.7 Gy (81%)/50 | 51.3 Gy (73%)/50 | NA |
| $PTV_{gr}$ | $D_{95} \geq 70$ Gy (100% of 70 Gy) Max. Dose $\leq 84$ Gy (120% of 70 Gy) | 70 Gy (100%) | 66.5 Gy (105%)/50 | 73.5 Gy (95%)/50 | NA |
| Spinal Cord | Max. Dose $\leq 45$ Gy | | 28 Gy (40%)/50 | | NA |
| Brainstem | Max. Dose $\leq 50$ Gy | | 35 Gy (50%)/50 | | NA |
| Parotid Gland | Mean Dose $\leq 26$ Gy | | 68 Gy (98%)/50 | | $\geq 21$ Gy (30%) to $\leq 30\%$ Volume/50 |
| Cochlea | Max. Dose $\leq 60$ Gy | | 56 Gy (80%)/50 | | NA |

FIG. 3

| | Per Protocol | Minor Variation | Major Variation |
|---|---|---|---|
| Total RT dose to PTV60 (to 95% of PTV60) | 60-64 Gy | 58-60 or 64-66 Gy | < 58 or > 66 Gy |
| Minimum dose ("cold spot") within PTV60, not including portion of PTV near (<8 mm) skin) | 56-60 Gy | 54-56 Gy | < 54 Gy |
| Maximum dose ("hot spot") within PTV60* | < 70 Gy | 70-72 Gy | > 72 Gy |
| Maximum dose ("hot spot" outside of PTV60) | < 66 Gy | 66-70 Gy | > 70 Gy |
| Definition of CTV60 | Base on case review by study chair. | | |
| Definition of PTV60 | Base on case review by study chair. | | |
| Total RT dose to spinal cord PRV (0.03 cc) | < 48 Gy | 48-50 Gy | > 50 Gy |
| Total RT dose to spinal cord PRV (0.01 cc) | < 50 Gy | 50-52 Gy | > 52 Gy |
| Definition of Spinal cord PRV | Base on case review by study chair. | | |
| Overall RT treatment time | | | > 50 days (without a medically appropriate indication for delay) |
| Non-Medically Indicated Treatment Interruptions | 0-2 | 2-4 | > 4 |

*Not including the region of PTV60 that falls within PTV66 (if applicable)

FIG. 4

6.4.3 *Critical Normal Structures*

DVH's must be generated for all critical normal structures and the unspecified tissues. Dose constraints to normal tissues will be as follows:

| | |
|---|---|
| Brainstem, optic nerves, chiasm | 54 Gy or 1% of the PTV cannot exceed 60Gy |
| Spinal Cord | 45 Gy or 1 cc *(if 1% is used, depends on length of the cord outlined)* of the PTV cannot exceed 50 Gy |
| Mandible and T-M joint | 70 Gy or 1 cc of the PTV cannot exceed 75 Gy |
| Temporal lobes | 60 Gy or 1 % of the PTV cannot exceed 65 Gy |

Unspecified tissue outside the targets: ≤ 100% of the dose prescribed to $PTV_{70}$. No more than 5% of the non-target tissue can receive greater than 70 Gy. Participants are strongly encourages to remain within these limits.

Table 1: Treatment for Radiation Sensitive Tumors

| Tumor | RTOG Guideline method | | | Present method | | | |
|---|---|---|---|---|---|---|---|
| | Prescribed radiation dose (cGy/day) | Percentage of PTV1 receiving > 110% of prescribed dose | Drop off rate beyond Tumor boundary | Predetermined average Safety Region radiation dose (cGy/day) | Boosted Region radiation dose (cGy/day) | Percentage of Boosted Region receiving > 110% of prescribed dose | Drop off rate beyond Tumor boundary |
| Squamous Carcinoma | 180-200 | <20% | 10%/mm | 200-315 | 220-350 | 70%-90% | 10%/mm |
| Adeno Carcinoma | 180-200 | <20% | 10%/mm | 200-315 | 220-350 | 70%-90% | 10%/mm |
| small cell Carcinoma | 180-200 | <20% | 10%/mm | 200-315 | 220-350 | 70%-90% | 10%/mm |
| Lymphoma Carcinoma | 180-200 | <20% | 10%/mm | 200-315 | 220-350 | 70%-90% | 10%/mm |
| Transitional cell Carcinoma | 180-200 | <20% | 10%/mm | 200-315 | 220-350 | 70%-90% | 10%/mm |

(PTV: planning target volume, which is equal to entire tumor region)

FIG. 12

Table 2: Treatment for Radiation Resistant Tumors

| Tumor | RTOG Guideline method | | | Present method | | | |
|---|---|---|---|---|---|---|---|
| | Prescribed radiation dose (cGy/day) | Percentage of PTV receiving > 110% of prescribed dose | Drop off rate beyond Tumor boundary | Predetermined average Safety Region radiation dose (cGy/day) | Boosted Region radiation dose (cGy/day) | Percentage of Boosted Region receiving > 110% of prescribed dose | Drop off rate beyond Tumor boundary |
| melanoma | 250 | <20% | 10%/mm | 275-400 | 300-450 | 70%-90% | 10%/mm |
| renal cancer | 250 | <20% | 10%/mm | 275-400 | 300-450 | 70%-90% | 10%/mm |

IMAGE-GUIDED RADIOTHERAPY FOR INTERNAL TUMOR BOOST

FIELD OF THE INVENTION

The present invention relates to image-guided radiotherapy, and more particularly to image-guided radiotherapy for tumor treatment.

BACKGROUND OF THE INVENTION

Radiotherapy is a proven modality for cancer cure similar to surgery for tumors of all sites. The probability to destroy the cancer locally is proportional to the radiation dose delivered to the cancer sites. Most often, the effectiveness of radiotherapy is limited by the radiation dose that can safely be delivered to the normal organs adjacent to the tumor. Serious complications may occur if the normal organs receive a radiation dose that exceeds their tolerance to radiation. Paralysis (spinal cord injury), blindness (optic nerve injury), stroke (brain injury), bleeding (blood vessels injury), inflammation of lungs (lungs injury) and bowels (bowels injury) may lead to death or seriously affect patient quality of life are well known complications of radiation treatment.

As such, prescribed doses are established in the literature to limit toxicity of the treatment to avoid complications. For example, Section 6.4.2.4 Radiation Therapy Oncology Group (RTOG) study number 0225: A Phase II Study of Intensity Modulated Radiation Therapy (IMRT)+/Chemotherapy for Nasopharyngeal Cancer specifies that "No more than 20% of any $PTV_{70}$ (the gross tumor volume with a 5 mm margin) will receive ≥110% of the prescribed dose." As used herein, the term "prescribed dose" means the conventional dose established in the literature for cancer cure with external beam radiotherapy alone or combined with chemotherapy for locally advanced head and neck cancer. As non-limiting examples, the "prescribed dose" for Oropharyngeal cancer, Oral cavity cancer, Laryngeal cancer, Hypopharyngeal cancer is about 7000 cGy, at about 200 cGy per day.

The present invention features an image-guided radiotherapy system for tumor treatment, wherein a boosted radiation dose is applied to a boost region within a tumor boundary.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features an apparatus for treatment of a tumor. In some embodiments, the apparatus comprises an imaging means for obtaining a three-dimensional visualized tumor image (100) to identify a tumor (110); one or more processors configured to delimit a tumor boundary (115) of the imaged tumor (110), and configured to designate a boosted region (120) within the tumor boundary, wherein a predetermined safety region (125) is between the boosted region and the tumor boundary (115) with a predetermined minimum distance (126) between the boosted region boundary and tumor boundary, wherein the boosted region (120) is more than 20% of the volume within the tumor boundary (115); and a radiation means configured to apply a boosted radiation dose of treatment within the boosted region (120) within the tumor boundary (115).

In some embodiments, the apparatus further comprises a radiation means configured to apply a prescribed radiation dose for the tumor boundary (115), wherein the prescribed radiation dose for the tumor boundary (115) is less than that at the boosted region (120). In some embodiments, the boosted region (120) is at least 70% of the volume of the volume within tumor boundary (115). In some embodiments; the boosted radiation dose is about 250 centiGray (cGy) or more. In some embodiments, the prescribed radiation dose is between 180 and 200 centiGray (cGy).

The present invention also features apparatus for treatment of a radiation resistant tumor, wherein the apparatus comprises an imaging means for obtaining a three-dimensional visualized tumor image (100); one or more processors configured to delimit the tumor boundary (115) of the imaged tumor (110) and configured to designate a boosted region (120) with the tumor boundary, wherein a predetermined safety region (125) is between the boosted region (120) and the tumor boundary (115) with a predetermined minimum distance between the boosted region boundary and tumor boundary (115), and wherein the boosted region (120) is more than 20% of the volume within the tumor boundary (115); and a radiation means configured to apply a boosted radiation dose of treatment within the boosted region (120) within the tumor boundary (115), wherein the radiation means is configured to apply radiation treatment for the safety region (125) with a first dose decreasing rate such that the radiation dose on the tumor boundary is a predetermined prescribed radiation dose and to apply radiation treatment beyond the tumor boundary and within a radiation boundary (140) with a second dose decreasing rate, wherein the predetermined prescribed radiation dose of treatment for the boundary of the tumor is less than the boosted radiation dose. In some embodiments, the boosted radiation dose is between 300 centiGray/day and 450 centiGray/day. In some embodiments, the average of the second dose decreasing rate is about 10% per millimeter.

The present invention also features the use of a system for treatment of a tumor. In some embodiments, the system comprises obtaining a three-dimensional visualized tumor image (100) to identify a tumor (110); delimiting a tumor boundary (115) of the imaged tumor (110), and designating a boosted region (120) within the tumor boundary, wherein a predetermined safety region (125) is between the boosted region and the tumor boundary (115) with a predetermined minimum distance (126) between the boosted region boundary and tumor boundary, wherein the boosted region (120) is more than 20% of the volume within the tumor boundary (115); and applying a boosted radiation dose of treatment within the boosted region (120) within the tumor boundary (115).

In some embodiments, the system further comprises applying a prescribed radiation dose to the tumor boundary (115), wherein the prescribed radiation dose for the tumor boundary (115) is less than that at the boosted region (120). In some embodiments, the boosted region (120) is at least 70% of the volume of the volume within tumor boundary (115). In some embodiments, the boosted radiation dose is about 250 centiGray (cGy) or more. In some embodiments, the prescribed radiation dose is between 180 and 200 centiGray (cGy).

The present invention also features the use of a system for treatment of a tumor, wherein the system comprises obtaining a three-dimensional visualized tumor image (100) to identify a tumor (110); delimiting the tumor boundary (115) of the imaged tumor (110) and designating a boosted region (120) with the tumor boundary, wherein a predetermined safety region (125) is between the boosted region (120) and the tumor boundary (115) with a predetermined minimum distance between the boosted region boundary and tumor boundary (115), and wherein the boosted region (120) is more than 20% of the volume within the tumor boundary (115); and applying via a radiation means a boosted radiation dose of treatment within the boosted region (120) within the tumor boundary (115), wherein the radiation means is configured to apply radiation treatment for the safety region (125) with a first dose decreasing rate such that the radiation dose on the tumor boundary is a predetermined prescribed radiation dose and to apply radiation treatment beyond the tumor boundary and within a radiation boundary (140) with a second dose decreasing rate, wherein the predetermined prescribed radiation dose of treatment for the boundary of the tumor is less than the boosted radiation dose. In some embodiments, the boosted radiation dose is between 300 centiGray/day and 450 centiGray/day. In some embodiments, the average of the second dose decreasing rate is about 10% per millimeter.

The present invention also features an image-guided radiotherapy method for treatment of a tumor. In some embodiments, the method comprises obtaining a three-dimensional visualized tumor image (100) to identify a tumor (110); identifying a tumor boundary (115) of the tumor (110); designating and applying a boosted radiation dose of treatment for a boost region (120) within the tumor boundary, wherein a predetermined safety region (125) is between the boosted region and the tumor boundary (115) with a predetermined minimum distance (126) between the boosted region boundary and tumor boundary, wherein the boosted region (120) is more than 20% of the volume within the tumor boundary (115); and repeating steps (a) through (c) for new treatment each time.

In some embodiments, the method further comprises designating a predetermined prescribed radiation dose of treatment for the boundary of the tumor, wherein the predetermined prescribed radiation dose is smaller than the boosted radiation dose; applying radiation treatment for the region safety region (125) with a first dose decreasing rate such that the radiation dose on the tumor boundary is the a predetermined prescribed radiation dose; and applying radiation treatment beyond the tumor boundary and within the radiation boundary (140) with a second dose decreasing rate; wherein the radiation treatment for the region safety region (125) and beyond the tumor boundary are applied together with the radiation treatment for the boost region (120).

In some embodiments, the tumor is Squamous Carcinoma, Adeno Carcinoma, small cell Carcinoma, Lymphoma Carcinoma or Transitional cell Carcinoma. In some embodiments, the boosted region (120) is at least 70% of the volume of the volume within tumor boundary (115). In some embodiments, the predetermined minimum distance between the boosted region boundary and tumor boundary is dependent on the boosted radiation dose and the prescribed radiation dose. In some embodiments, the boosted radiation dose is about 250 centiGray (cGy) or above. In some embodiments, the prescribed radiation dose is between 180 and 200 centiGray (cGy). In some embodiments, the average of the second dose decreasing rate is about 10% per millimeter. In some embodiments, the method further includes identifying a radiation sensitive normal organ (130) near the tumor boundary (115) and further increasing a distance (128) within the tumor (110) near the organ (130) to avoid excessive radiation influence on the radiation sensitive normal organs (130).

The present invention also features an image-guided radiotherapy method for treatment of a radiation resistant tumor. In some embodiments, the method comprises obtaining a three-dimensional visualized tumor image (100); identifying the boundary (115) of the tumor (110); designating and applying a boosted radiation dose of treatment for a boost region (120) within the tumor boundary, wherein a predetermined safety region (125) is between the boosted region and the tumor boundary (115) with a predetermined minimum distance between the boosted region boundary and tumor boundary, wherein the boosted region (120) is more than 20% of the volume within the tumor boundary (115); designating a predetermined prescribed radiation dose of treatment for the boundary of the tumor, wherein the predetermined prescribed radiation dose is smaller than the boosted radiation dose; applying radiation treatment for the region safety region (125) with a first dose decreasing rate such that the radiation dose on the tumor boundary is the a predetermined prescribed radiation dose; applying radiation treatment beyond the tumor boundary and within the radiation boundary (140) with a second dose decreasing rate; and repeat steps (a) thru (f) for new treatment each time.

In some embodiments, the predetermined minimum distance (126) between the boosted region boundary and tumor boundary is dependent on the boosted radiation dose and the prescribed radiation dose. In some embodiments, the radiation resistant tumor is melanoma or renal cancer. In some embodiments, the boosted radiation dose is between 300 centiGray/day and 450 centiGray/day. In some embodiments, the average of the second dose decreasing rate is about 10% per millimeter. In some embodiments, the method further includes identifying a radiation sensitive normal organ (130) near the tumor boundary (115) and further increasing the distance (126) within the tumor (110) near the organ (130) to avoid excessive radiation influence on the normal organs (130).

The present invention features an image-guided radiotherapy system for tumor treatment. In some embodiments, the system comprises obtaining a three-dimensional visualized tumor image, delimiting (e.g., identifying) the boundary of the tumor; and designating and applying a boosted radiation dose of treatment for a boost region within the tumor boundary. A predetermined safety region is between the boosted region and the tumor boundary with a predetermined minimum distance between the boosted region boundary and tumor boundary.

In some embodiments, the system comprises designating a predetermined prescribed radiation dose of treatment for the boundary of the tumor, wherein the predetermined prescribed radiation dose is smaller than the boosted radiation dose. In some embodiments, the system comprises applying radiation treatment for the safety region with a first dose decreasing rate such that the radiation dose on the tumor boundary is the predetermined prescribed radiation dose. In some embodiments, the system comprises applying radiation treatment beyond the tumor boundary and within the radiation boundary with a second dose decreasing rate.

BRIEF DESCRIPTION OF THE DRAWINGS

FIG. 3 shows the Memorial Sloan Kettering Cancer Center (MSKCC) Clinical Dose Limits and Inverse Planning Algorithm Constraints for Primary Nasopharynx Tumors.

FIG. 4 shows the compliance criteria of radiation treatment adopted in Radiation Therapy Oncology Group (RTOG) study number 0920.

DESCRIPTION OF PREFERRED EMBODIMENTS

Referring now to FIG. 1-13, the present invention features image-guided radiotherapy systems for tumor treatment.

Figure 1:
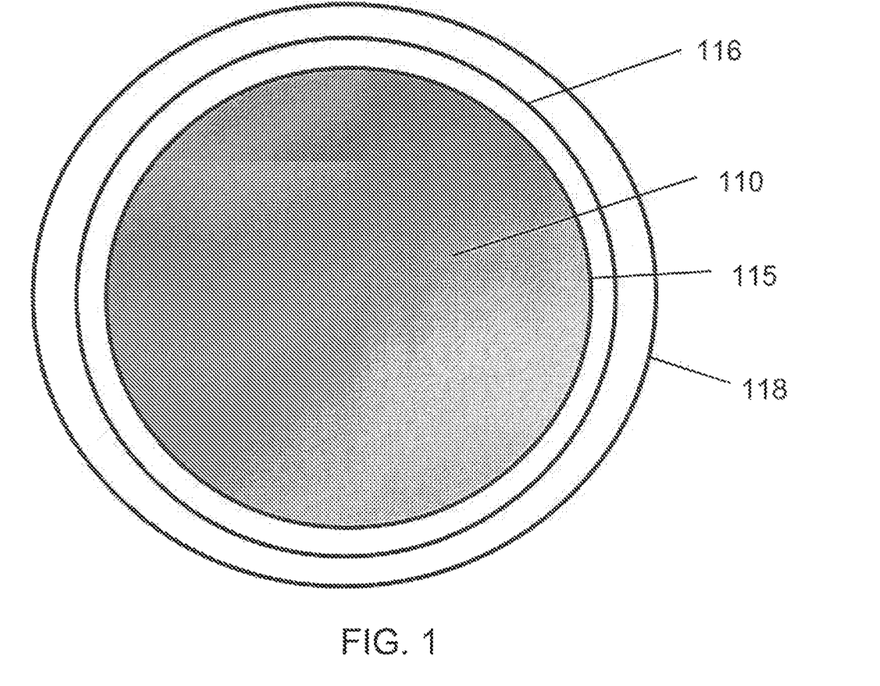
FIG. 1 shows a schematic view of gross tumor volume (GTV), clinical tumor volume (CTV), and planning target volume (PTV).

FIG. 1 shows a schematic view for a gross tumor volume (GTV), a clinical tumor volume (CTV), and planning target volume (PTV). The planning target volume (PTV) is the traditional radiation treatment volume and is beyond the tumor boundary. In FIG. 1, a tumor (110) has a tumor boundary (115) that encloses the gross tumor boundary. Clinical tumor volume (CTV) is enclosed by a gross tumor volume (GTV) boundary (116). The planning tumor volume (PTV) is enclosed by a PTV boundary (118).

Figure 2:
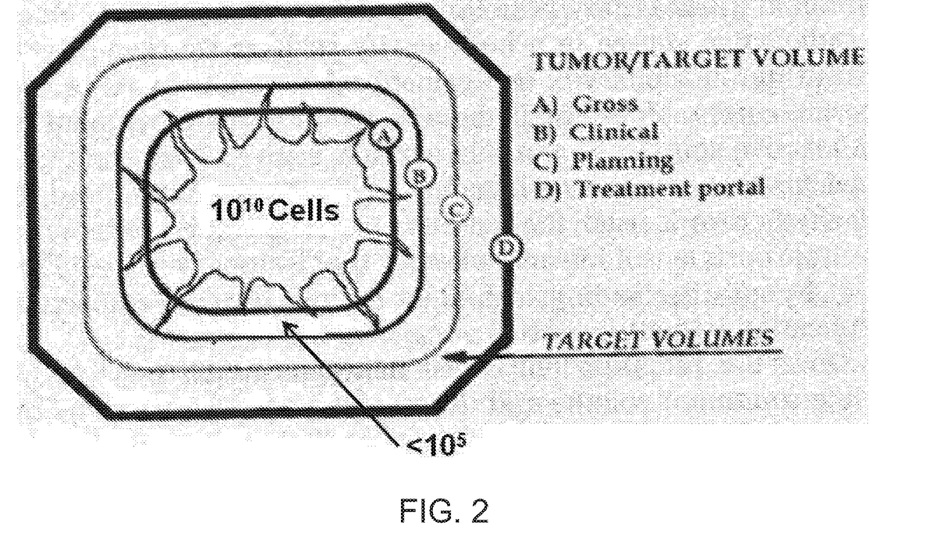
FIG. 2 is a schematic representation of "volumes" in radiation therapy. The treatment portal volume includes the tumor volume, potential areas of local and regional microscopic disease around the tumor, and a margin surrounding normal tissue. (Modified from Perez C A, Purdy J A. Rationale for Treatment Planning in Radiation Therapy. In: Levitt S H, Khan F M, Potish R A, eds. *Levitt and Tapley's Technological Basis of Radiation Therapy: Practical Clinical Applications,* $2^{nd}$ ed. Philadelphia: Lea & Febiger, 1992; with permission.)

FIG. 2 shows a schematic representation of "volumes" in radiation therapy in terms of Gross Target Volume, Clinical Target Volume, Planning Target Volume (from Page 5, Chapter 1: The Discipline of Radiation Oncology, Book: Perez and Brady's Principles and Practice of Radiation Oncology, 5th Edition, published by Lippincott Williams & Wilkins with ISBN-10: 078176369X). This figure shows that the planning target volume (PTV) (118) is beyond the tumor boundary (115).

FIG. 3 shows the Memorial Sloan-Kettering Cancer Center (MSKCC) Clinical Dose Limits and Inverse Planning Algorithm Constraints for Primary Nasopharynx Tumors, excerpted from "A practical guide to intensity-modulated radiation therapy" (Medical Physics Pub., 2003, ISBN: 1930524137), Chapter 10: IMRT for head and neck Cancer, Table 10.3, page 201. The table regulates that the maximum radiation dose is 105%.

FIG. 4 shows the compliance criteria of radiation treatment in Radiation Therapy Oncology Group (RTOG) study number 0920: A Phase III Study of Postoperative Radiation Therapy (IMRT)+/–Cetuximab for Locally-Advanced Resected Head and Neck Cancer, section 6.7, page 27. The criteria lists in Row 1 that any Radiation dose (RT)>66 Gy as a major variation should be avoided at any rate. The 66 Gy corresponds to a 10% increase over planning target volume (PTV) 60 Gy.

Figure 5:
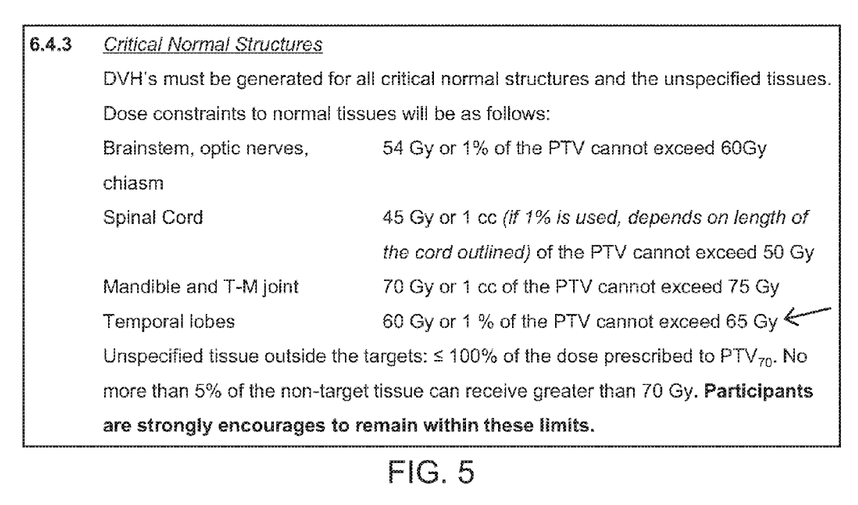
FIG. 5 shows the Critical Normal Structures in Radiation Therapy Oncology Group (RTOG) study number 0225.

FIG. 5 shows the Critical Normal Structures in Radiation Therapy Oncology Group (RTOG) study number 0225: A Phase II Study of Intensity Modulated Radiation Therapy (IMRT)+/Chemotherapy for Nasopharyngeal Cancer, section 6.4.3 Critical Normal Structures, page 7. The Critical Normal Structures discloses that 60 Gy or 1% of the PTV cannot exceed 65 Gy (which is close to 10% increase over PTV 60 Gy radiation.)

Figure 6:
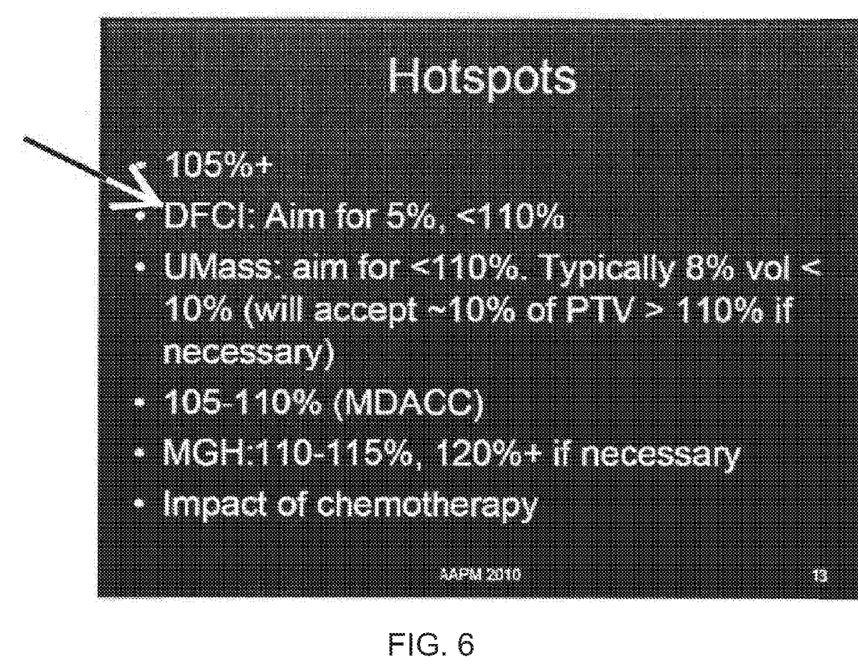
FIG. 6 shows the hotspot radiation regulation in a presentation (slide 13) of a research taken at Dana-Farber/Brigham 8, Women's Cancer Center and Harvard Medical School.

FIG. 6 shows the hotspot radiation regulation in a presentation (slide 13) of a research taken at Dana-Farber Brigham & Women's Cancer Center and Harvard Medical School ("Variability in planning criteria and plan evaluation," Laurence Court, the American Association of Physicists in Medicine annual meeting 2010). The slide shows the aiming for hotspots radiation is limited to <110% of the radiation dose.

The present invention features image-guided radiotherapy systems for providing higher doses (as compared to the current doses in the art) of radiation for tumor tissues. The systems may help to avoid excessive radiation to normal tissues.

Figure 7:
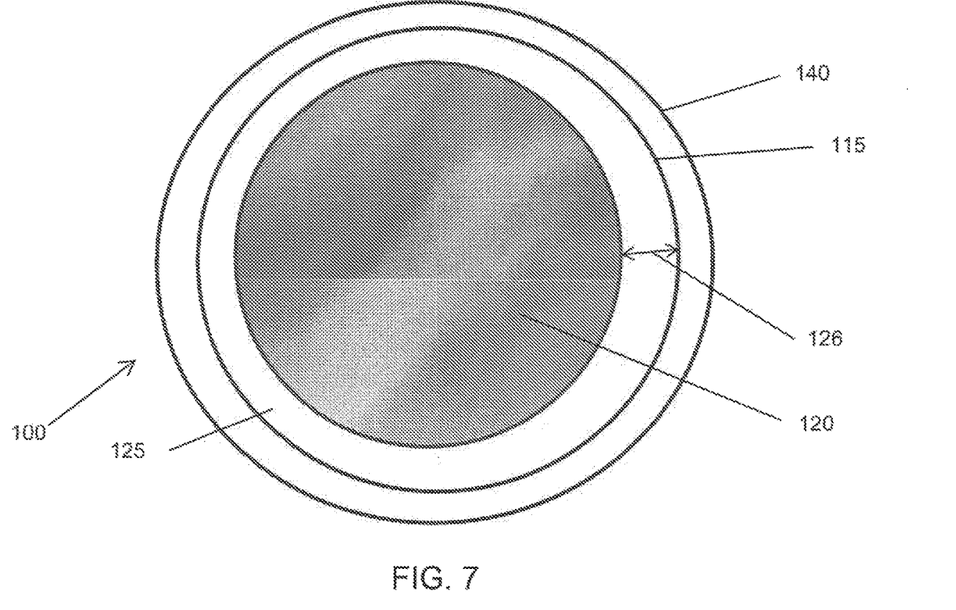
FIG. 7 shows a schematic view of a tumor boundary and boosted treatment region of the present invention.

The system comprises (a) obtaining a three-dimensional visualized tumor image (100); (b) identifying the boundary (115) of the tumor (110); and (c) designating and applying a boosted radiation dose of treatment for a boost region (120) within the tumor boundary. A predetermined safety region (125) is between the boosted region and the tumor boundary (115) with a predetermined minimum distance (126) between the boosted region boundary and tumor boundary. Steps (a) through (c) are repeated for new treatment each time.

In some embodiments, the boosted region (120) is more than about 20% of the volume within the tumor boundary (115). In some embodiments, the boosted region (120) is more than about 10% of the volume within the tumor boundary (115).

In some embodiments, the boosted region (120) is more than about 30% of the volume within the tumor boundary (115). In some embodiments, the boosted region (120) is more than about 40% of the volume within the tumor boundary (115). In some embodiments, the boosted region (120) is more than about 50% of the volume within the tumor boundary (115). In some embodiments, the boosted region (120) is more than about 60% of the volume within the tumor boundary (115). In some embodiments, the boosted region (120) is more than about 70% of the volume within the tumor boundary (115). In some embodiments, the boosted region (120) is more than about 80% of the volume within the tumor boundary (115). In some embodiments, the boosted region (120) is more than about 90% of the volume within the tumor boundary (115).

Figure 11:
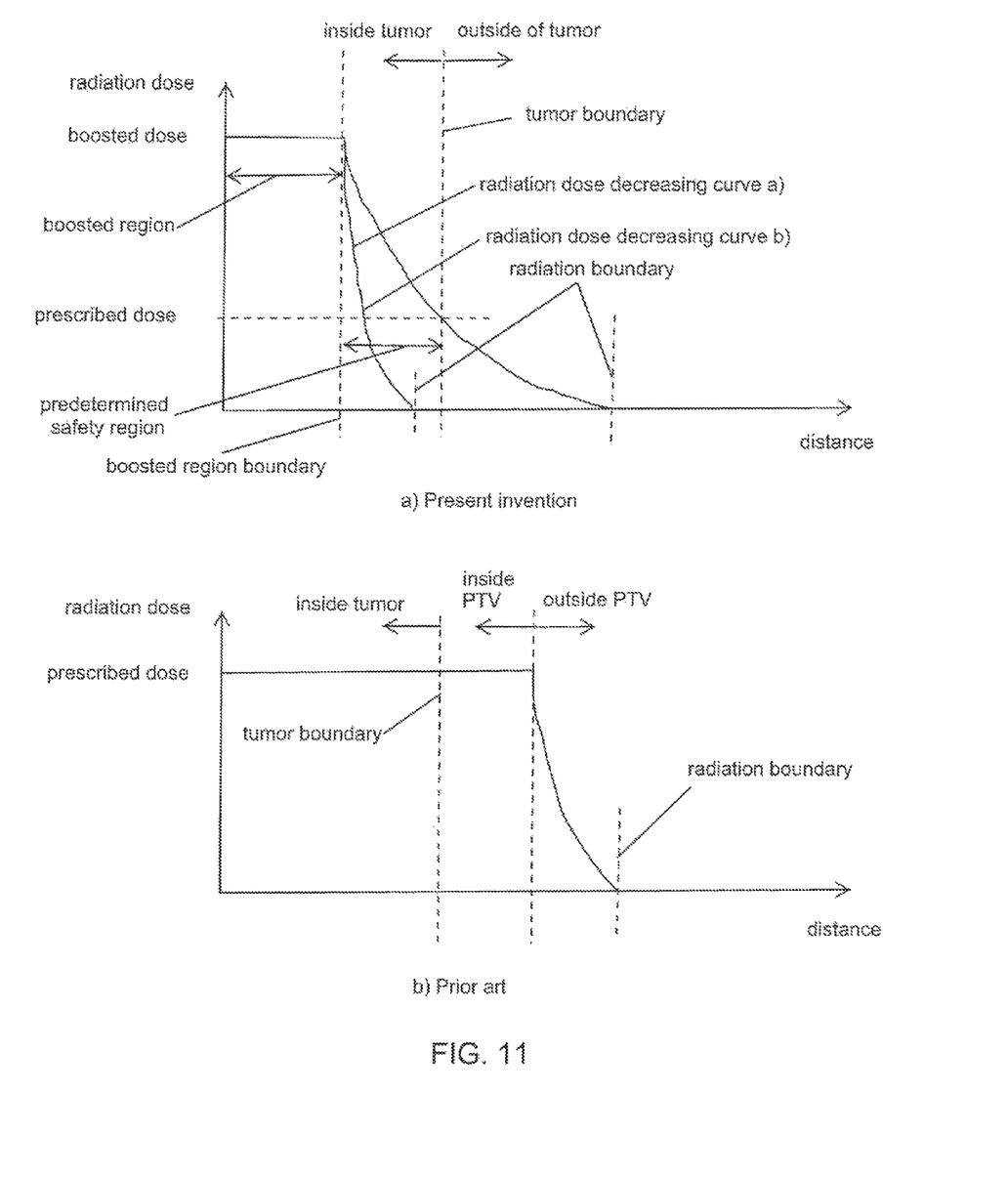
FIG. 11 shows a radiation dose comparison between a traditional method and the present method.

In some embodiments, the system further comprises designating a predetermined prescribed radiation dose of treatment for the boundary of the tumor, wherein the predetermined prescribed radiation dose is smaller than the boosted radiation dose. In some embodiments, the system further comprises applying radiation treatment for the safety region (125) with a first dose decreasing rate such that the radiation dose on the tumor boundary is the a predetermined prescribed radiation dose. In some embodiments, the system further comprises applying radiation treatment beyond the tumor boundary and within the radiation boundary (140) with a second dose decreasing rate. In some embodiments, the radiation treatment for the safety region (125) and beyond the tumor boundary is applied together with the radiation treatment for the boosted region (120). The radiation dose decreasing curve can be viewed in FIG. 11A. In some embodiments, the radiation dose decreases rapidly beyond boost region boundary and reduces to zero within the safety region (125). The radiation dose decreasing curve can be viewed in FIG. 11B.

In some embodiments, the tumor is a radiation sensitive tumor, such as Squamous Carcinoma, Adeno Carcinoma, small cell Carcinoma, Lymphoma Carcinoma or Transitional cell Carcinoma. In some embodiments, the featured image-guided radiotherapy system for tumor treatment is applicable to treatment of neck node less than 3 centimeters (cm) in diameter. In some embodiments, the featured image-guided radiotherapy system for tumor treatment is applicable to treatment of neck nodes with diameter between 3 cm and 6 cm. In some embodiments, the featured image-guided radiotherapy system for tumor treatment is applicable for effective treatment of neck nodes larger than 6 centimeter (cm) in diameter. In some embodiments, the featured image-guided radiotherapy system for tumor treatment is applicable to treatment of locally advanced head and neck cancer that have not spread to distant organs. In some embodiments, the featured image-guided radiotherapy system for tumor treatment is applicable to treatment of locally advanced tumor invading the adjacent organs, such as the spinal cord, blood vessels, brachial plexus or other nerve roots, optic chiasm, optic nerves, pituitary, eyes, small and large bowels, trachea, major airways, kidneys, liver, bladder, and genital organs. In some embodiments, the featured image-guided radiotherapy system for tumor treatment is applicable for effective treatment of a tumor larger than 6 centimeter (cm) in diameter.

As an illustration, a locally advanced head and neck cancer may erode into the spinal canal and threaten to produce paralysis through compression of the spinal cord. The current technique allows for shrinkage of the tumor away from the spinal cord because of the high dose gradient inside the tumor while the spinal cord receives a radiation dose that does not exceed the threshold for damage to the spinal cord. A similar technique can be used to spare the eyes and optic nerves from excessive radiation that can produce blindness when the tumor invades into the orbits. Some tumors such as nasopharyngeal cancers have the propensity to invade the brain through the base of skull and compress the cranial nerves and brain producing paralysis of the face, blindness, deafness, and stroke. The current radiotherapy technique allows for decompression of the nerves when the tumor shrink and may potentially save the patient life and/or quality of life because these tumors are inoperable and requires high radiation dose for cure. This new radiotherapy technique can be applied to any tumor sites in the body because it kills the tumor from the inside and spare the adjacent radiosensitive organs.

In some embodiments, the featured image-guided radiotherapy system for tumor treatment is applicable to treatment of locally advanced head and neck cancer with serious toxicity during radiation.

Radiation therapy dose is generally measured in Gray or centigray (cGy) (1 Gray=100 cGy). Radiation dose delivered a day is called fraction and conventionally limited to 180-200 cGy a day. In patients with known radio-resistant tumors such as melanoma or renal cancer, radiation dose is increased to 250 cGy or more because of the tumor's ability to repair radiation damage. Most tumors often require a total dose of 7000 cGy delivered over six to seven weeks of treatment for possible local control.

In some embodiments, the total energy delivered during one treatment cycle, such as six to seven weeks, with the featured tumor treatment of internal boost, is equal to the total energy regulated or specified by the Radiation Therapy Oncology Group (RTOG) with one radiation dose level applied to the planning treatment volume (PTV). In some embodiments, the total energy delivered during one treatment cycle, such as six to seven weeks, with the featured tumor treatment of internal boost, is larger than the total energy regulated or specified by the Radiation Therapy Oncology Group (RTOG) with one radiation dose level applied to the planning treatment volume (PTV). With the featured tumor treatment of internal boost, the radiation energy may be tuned to focus within internal part of the tumor, rather than distributed uniformly around planning treatment volume, which includes the tutor volume itself and beyond. The total energy is referred as the total radiation energy absorbed for the entire volume where radiation treatment is received.

In some embodiments, the total energy delivered during one treatment cycle, such as six to seven weeks, with the featured tumor treatment of internal boost is equal to the total energy with the traditional radiation treatment method using one radiation dose level applied to the planning treatment volume (PTV). In some embodiments, the total energy delivered during one treatment cycle, such as six to seven weeks, with the featured tumor treatment of internal boost is larger than the total energy with the traditional radiation treatment method using one radiation dose level applied to the planning treatment volume (PTV). With the featured tumor treatment of internal boost, the radiation energy may be tuned to focus within internal part of the tumor, rather than distributed uniformly around planning treatment volume, which includes the tutor volume itself and beyond. The total energy is referred as the total radiation energy absorbed for the entire volume where radiation treatment is received.

In some embodiments, the boosted region (120) is more than 20% of the volume within the tumor boundary (115). In some embodiments, the boosted region (120) is more than 30% of the volume within the tumor boundary (115). In some embodiments, the boosted region (120) is more than 40% of the volume within the tumor boundary (115). In some embodiments, the boosted region (120) is more than 50% of the volume within the tumor boundary (115). In some embodiments, the boosted region (120) is more than 60% of the volume within the tumor boundary (115). In some embodiments, the boosted region (120) is at least 70% of the volume within the tumor boundary (115). In some embodiments, the boosted region (120) is between 70% and 90% of the volume within the tumor boundary (115). In some embodiments, the boosted region (120) is between 70% and 80% within the tumor boundary (115). In some embodiments, the boosted region (120) is between 80% and 90% within the tumor boundary (115).

In some embodiments, the prescribed radiation dose is between 180 and 200 centiGray (cGy), while the boosted radiation dose is about 250 centiGray (cGy) or above. In some embodiments, the average of the second dose decreasing rate is about 10% per millimeter.

In some embodiments, the average radiation dose in the safety region (125) is about 5% less than the radiation dose in the boosted region (120). In some embodiments, the average radiation dose in the safety region (125) is about 10% less than the radiation dose in the boosted region (120). In some embodiments, the average radiation dose in the safety region (125) is about 15% less than the radiation dose in the boosted region (120). In some embodiments, the average radiation dose in the safety region (125) is about 20% less than the radiation dose in boost region (120). In some embodiments, the average radiation dose in the safety region (125) is about 25% less than the radiation dose in the boosted region (120). In some embodiments, the average radiation dose in the safety region (125) is about 30% less than the radiation dose in the boosted region (120). In some embodiments, the average radiation dose in the safety region (125) is more than about 30% less than the radiation dose in the boost region (120).

In some embodiments, the predetermined distance between the boosted region boundary and tumor boundary is uniform. In some embodiments, the predetermined distance between the boosted region boundary and tumor boundary is non-uniform. The predetermined minimum distance (126) between the boosted region boundary and tumor boundary is dependent on the boosted radiation dose and the prescribed radiation dose.

In some embodiments, the predetermined minimum distance (126) is about 1 centimeter (cm). In some embodiments, the predetermined minimum distance (126) is between about 0.05 and 0.1 cm. In some embodiments, the predetermined minimum distance (126) is between about 0.1 and 0.25 cm. In some embodiments, the predetermined minimum distance (126) is between about 0.25 and 0.5 cm. In some embodiments, the predetermined minimum distance (126) is between about 0.5 and 0.75 cm. In some embodiments, the predetermined minimum distance (126) is between about 0.75 and 1 cm. In some embodiments, the predetermined minimum distance (126) is between about 1 and 2 cm. In some embodiments, the predetermined minimum distance (126) is between about 2 and 5 cm. In some embodiments, the predetermined minimum distance (126) is between 0.1 and 0.5 cm. In some embodiments, the predetermined minimum distance (126) is between 0.5 and 1 cm.

Figure 8:
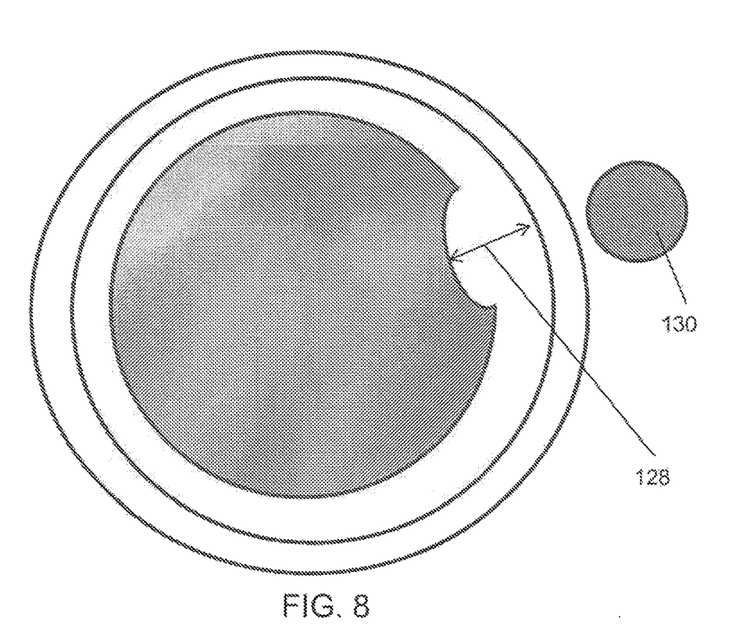
FIG. 8 shows a schematic view of a tumor boundary and boosted treatment region when a radiation sensitive normal organ is near the tumor boundary of the present invention.

In some embodiments, the system further comprises identifying a radiation-sensitive normal organ (130) near the tumor boundary (115) and further increasing a distance (128) within the tumor (110) near the organ (130) to avoid excessive radiation influence on the radiation sensitive normal organs (130). In some embodiments, the predetermined minimum distance is dependent on importance level and radiation sensitivity level of the normal organ (130).

Similarly, in the case of radiation resistant tumor treatment, the predetermined minimum distance (126) in the between the boosted region boundary and tumor boundary is dependent on the boosted radiation dose and the prescribed radiation dose. In some embodiments, the boosted radiation dose is between 300-450 centiGray/day or above and the second dose decreasing rate is 10% per millimeter.

Similarly, in the case of radiation resistant tumor treatment, the system may further comprise identifying a radiation sensitive normal organ (130) near the tumor boundary (115) and further increasing the distance (126) within the tumor (110) near the organ (130) to avoid excessive radiation influence on the normal organs (130).

Figure 9:
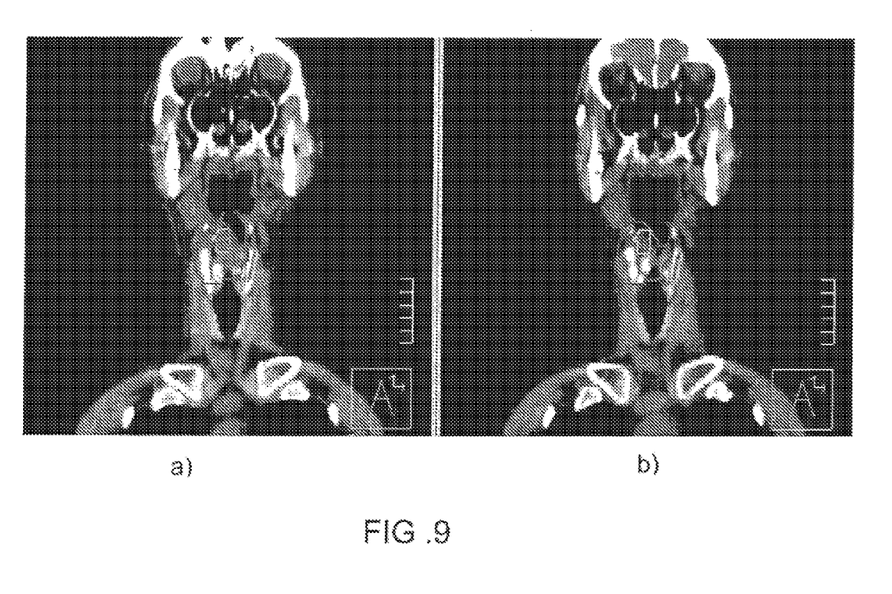
FIG. 9 shows a front view comparison of radiation treatment results of the present method before and after treatment.
Figure 10:
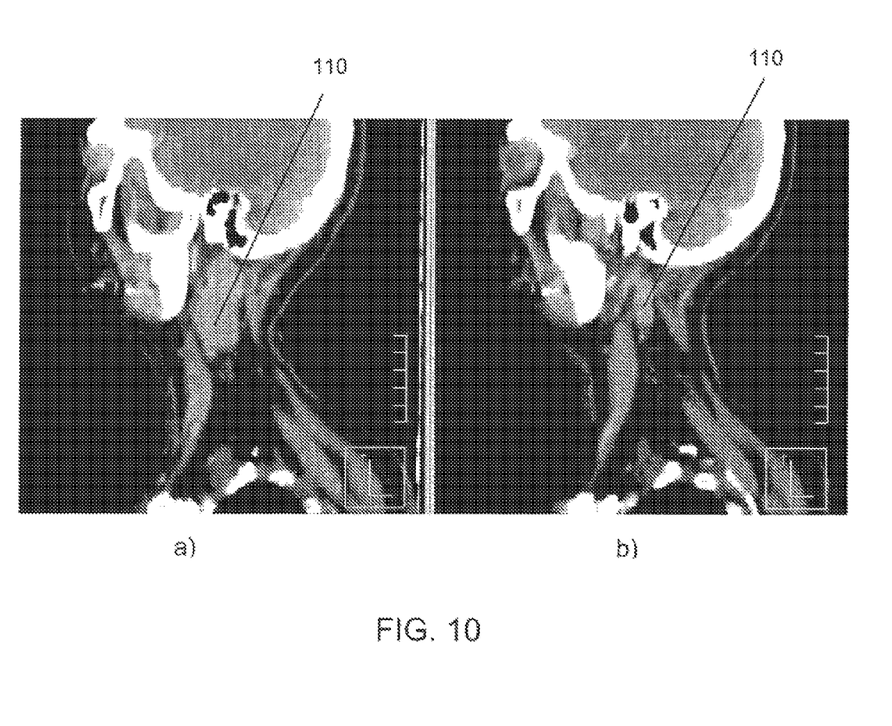
FIG. 10 shows a side view comparison of radiation treatment results before and after treatment.

The experimental comparison of treatment using the present method before and after treatment is shown in FIGS. 9 and 10. FIG. 9A and FIG. 10A show the image before treatment in front and side view, respectively. FIG. 9B and FIG. 10B show the image after treatment in front and side view, respectively. The outer line (red line) represents the tumor treated to 200 centigray (cGy) a day. The inner line (pink line) represents the internal boost treated 220 cGy a day (110%). At least 70% of the tumor received 110%. Without wishing to limit the present invention to any theory or mechanism, it is believed that the tumor shrinks from the high radiation dose.

Figure 12:
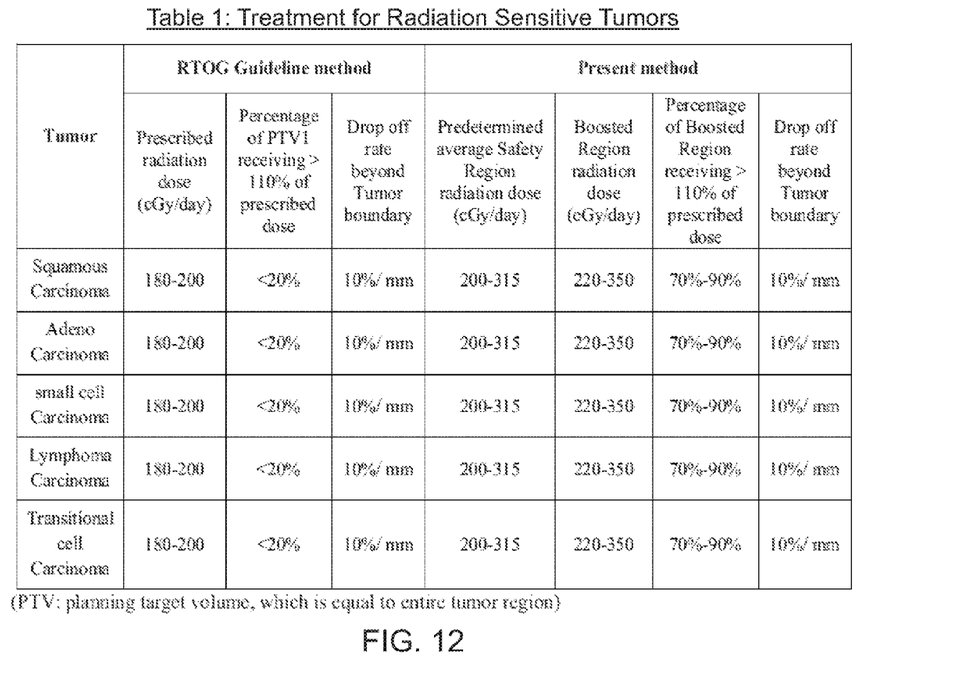
FIG. 12 shows some typical radiation dose for typical RTOG Guideline method and the present method for Radiation Sensitive Tumors.
Figure 13:
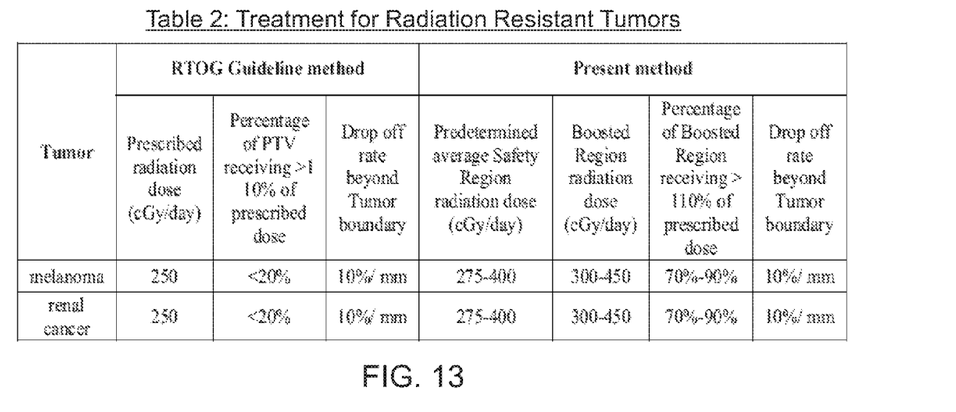
FIG. 13 shows some typical radiation dose for typical RTOG Guideline method and the present method for Radiation Resistant Tumors.

Table 1 in FIG. 12 and Table 2 in FIG. 13 show some typical radiation dose for typical RTOG Guideline method and the present method.

The radiation for use in accordance with the present invention may be delivered using any appropriate beam radiation techniques, for example, Intensity Modulated Radiotherapy (IMRT) and Image-guided radiotherapy (GRT). With IGRT the clinician can see the pictures of the tumor daily. With IMRT, the clinician cannot see the pictures. Systems which can be used in accordance with the present invention include but are not limited to systems made by Tomotherapy, Varian, Siemens, Elekta, Toshiba and the like. Varian has Varian True Beam, Rapid Arc, Varian EX or IX.

The present invention features an apparatus for treatment of a tumor. In some embodiments, the apparatus comprises an imaging means for obtaining a three-dimensional visualized tumor image (100) to identify a tumor (110). An imaging means may comprise a scanner, for example a MRI scanner. The imaging means is not limited to a MRI scanner. In some embodiments, the apparatus comprises one or more processors configured to delimit a tumor boundary (115) of the imaged tumor (110). The processors may be configured to designate a boosted region (120) within the tumor boundary, wherein a predetermined safety region (125) is between the boosted region and the tumor boundary (115) with a predetermined minimum distance (126) between the boosted region boundary and tumor boundary, wherein the boosted region (120) is more than 20% of the volume within the tumor boundary (115). Processors are well known to one of ordinary skill in the art. In some embodiments, the apparatus comprises a radiation means configured to apply a boosted radiation dose of treatment within the boosted region (120) within the tumor boundary (115). A radiation means may comprise a radiation source (e.g., with a radioisotope, etc.). A radiation means may comprise a system adapted to emit radiation to a target, e.g., a tumor. Medical systems for delivering radiation to targets are known in the art. In some embodiments, a human performs the delimiting of a tumor boundary (115) of the imaged tumor (110). In some embodiments, a human defines a boosted region (120) within the tumor boundary, wherein a predetermined safety region (125) is between the boosted region and the tumor boundary (115) with a predetermined minimum distance (126) between the boosted region boundary and tumor boundary, wherein the boosted region (120) is more than 20% of the volume within the tumor boundary (115).

CLINICAL EXAMPLE 1

In this example, a 75-year old white male patient with a stage T4N2M0 laryngeal cancer (locally advanced tumor that spread to the cervical lymph nodes producing enlargement of the lymph node between 3 to 6 cm and without distant metastases) had been treated with a prescribed tumor dose of 7000 cGy at 200 cGy per day and boosted radiation level of 7700 cGy at 220 cGy/day for 35 days. The original tumor was obstructing the airway and threatened to asphyxiate the patient. After 20 days of treatment (or 4000 cGy prescribed tumor dose and 4400 cGy boosted radiation dose for boosted region), the tumor shrunk to 20% of its initial size allowing the patient to breathe. The treatment has no complication observed. Boosted region is about 80% of the tumor volume. The treatment is repeated daily. At each new treatment, a new scanning for tumor location and size have been done before applying of radiation treatment to ensure the accuracy of the dose delivered. The cancer disappeared after treatment both on clinical exams and diagnostic X-rays. The patient has a normal voice following treatment and remains free of cancer 16 months following treatment.

CLINICAL EXAMPLE 2

In this example, a 71-year-old patient with a stage T4N0M0 (locally advanced tumor that did not spread to the cervical lymph nodes and distant organs) oropharyngeal cancer had been treated with a tumor dose of 7000 cGy (200 cGy a day) and boosted radiation level of 7700 cGy at 220 cGy/day for 35 days. The tumor extended upward from the soft palate to the nasopharynx, anteriorly to the hard palate and oral cavity, and downward to the base of tongue preventing patient from swallowing food. After 15 days of treatment (or 3000 cGy prescribed tumor dose treatment and 3300 cGy boosted radiation dose for boosted region), the tumor had reduced to 90% of its initial size allowing the patient to swallow again. The treatment has no complication observed. Boosted region is about 85% of the tumor volume. The treatment is repeated daily. At each new treatment, a new scanning for tumor location and size have been done before applying of radiation treatment to verify treatment accuracy. The cancer completely disappeared at the end of radiation treatment. The patient is currently disease free 21 months following treatment and is able to eat and drink normally without any complications.

CLINICAL EXAMPLE 3

In this example, a 56-year-old white male with a stage T4N3M0 oropharyngeal cancer (locally advanced tumor that invaded the cervical lymph nodes producing enlargement of the lymph nodes more than 6 cm and without distant metastases) had been treated with a dose of 7000 cGy (200 cGy/day) to the tumor and bilateral lymph nodes and boosted radiation level of 7700 cGy (220 cGy/day for 35 days. Original neck nodes measured 8 cm in diameter. After 20 days of treatment (or 4000 cGy prescribed tumor radiation dose and 4400 cGy boosted radiation dose for boosted region), the neck nodes had reduced to a diameter about 3 cm. The treatment has no complication observed. Boosted region is about 70% of the tumor volume and neck nodes. The treatment is repeated each day. At each new treatment, a new scanning for tumor location and size have been done before applying of radiation treatment to verify treatment accuracy. The tumor and neck nodes completely disappeared following treatment and the patient is cancer-free five months after treatment without any complications.

As used herein, the term "about" refers to plus or minus 10% of the referenced number. For example, an embodiment wherein a radiation dose is about 250 centiGray (cGy) includes radiation dose between 225 and 275 centiGray (cGy).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. An image-guided radiotherapy method for treatment of a tumor, the method comprising:
   a) obtaining a three-dimensional visualized tumor image to identify a tumor;
   (b) identifying a tumor boundary of the tumor;
   c) designating and applying a boosted radiation dose of treatment to a boosted region within the tumor boundary, wherein a predetermined safety region is between the boosted region and the tumor boundary with a predetermined minimum distance between a boundary of the boosted region and the tumor boundary, wherein the boosted region is more than 20% of a volume within the tumor boundary, wherein the boosted radiation dose of treatment has a first dose decreasing rate, wherein the boosted radiation dose of treatment is applied to the boosted region such that the boosted radiation dose is zero within the predetermined safety region;
   d) designating a first radiation treatment, wherein the first radiation treatment is a predetermined prescribed radiation dose of treatment for the tumor boundary, wherein the predetermined prescribed radiation dose is smaller than the boosted radiation dose;
   e) applying a second radiation treatment to the predetermined safety region, wherein the second radiation treatment has a second dose decreasing rate, wherein the second radiation treatment is applied to the predetermined safety region such that the tumor boundary receives the predetermined prescribed radiation dose; and
   applying a third radiation treatment, wherein the third radiation treatment is applied to a region beyond the tumor boundary and within a radiation boundary, wherein the third radiation treatment has a third dose decreasing rate; wherein the second radiation treatment and the third radiation treatment are applied together with the boosted radiation dose of treatment.

2. An image-guided radiotherapy method for treatment of a tumor, the method comprising:
   a) obtaining a three-dimensional visualized tumor image to identify a tumor;
   (b) identifying a tumor boundary of the tumor;
   (c) designating and applying a boosted radiation dose of treatment to a boosted region within the tumor boundary, wherein a predetermined safety region is between the boosted region and the tumor boundary with a predetermined minimum distance between a boundary of the boosted region and the tumor boundary, wherein the boosted region is more than 20% of a volume within the tumor boundary, wherein the boosted radiation dose of treatment has a first dose decreasing rate, wherein the boosted radiation dose of treatment is applied to the boosted region such that the boosted radiation dose is zero within the predetermined safety region;

(d) designating a first radiation treatment, wherein the first radiation treatment is a predetermined prescribed radiation dose of treatment for the tumor boundary, wherein the predetermined prescribed radiation dose is smaller than the boosted radiation dose;

e) applying a second radiation treatment to the predetermined safety region, wherein the second radiation treatment has a second dose decreasing rate, wherein the second radiation treatment is applied to the predetermined safety region such that the tumor boundary receives the predetermined prescribed radiation dose; and (f) applying a third radiation treatment, wherein the third radiation treatment is applied to a region beyond the tumor boundary and within a radiation boundary, wherein the third radiation treatment has a third dose decreasing rate; wherein the second radiation treatment and the third radiation treatment are applied together with the boosted radiation dose of treatment, wherein the predetermined minimum distance between the boosted region boundary and the tumor boundary is dependent on the boosted radiation dose and the prescribed radiation dose.

* * * * *